United States Patent [19]

Hohlweg et al.

[11] Patent Number: 5,721,260

[45] Date of Patent: Feb. 24, 1998

[54] HETEROCYCLIC COMPOUNDS

[75] Inventors: Rolf Hohlweg, Kvistgaard; Knud Erik Andersen, Smørum; Tine Krogh Jørgensen, Herlev; Peter Madsen, Bagsvaerd; Henrik Sune Andersen, København, all of Denmark

[73] Assignee: Novo Nordisk A/S, Bagsvaerd, Denmark

[21] Appl. No.: 628,042

[22] Filed: Apr. 4, 1996

[30] Foreign Application Priority Data

Apr. 7, 1995 [DK] Denmark .................. 0414/95

[51] Int. Cl.$^6$ .......................... A61K 31/40; A61K 31/38; A61K 31/35

[52] U.S. Cl. .......................... 514/428; 514/437; 514/454; 549/26; 549/223; 548/525; 548/528

[58] Field of Search .................. 548/518, 525, 548/528; 514/422, 428, 437, 454; 549/26, 223

[56] References Cited

FOREIGN PATENT DOCUMENTS 0 221 572    5/1987    WIPO.

OTHER PUBLICATIONS

Pavia et al., J. Med. Chem., vol. 35, pp. 4238–4248, (1992).
Falch et al., Drug Design & Delivery, vol. 4, pp. 205–215, (1989).

*Primary Examiner*—Amelia Averill Owens
*Attorney, Agent, or Firm*—Steve T. Zelson, Esq.; Elias J. Lambiris, Esq.

[57] ABSTRACT

The present invention relates to novel N-substituted azaheterocyclic carboxylic acids and esters thereof in which a substituted alkyl chain forms part of the N-substituent or salts therefor, to methods for their preparation, to compositions containing them, and to their use for the clinical treatment of painful, hyperalgesic and/or inflammatory conditions in which C-fibers play a pathophysiological role by eliciting neurogenic pain or inflammation.

20 Claims, No Drawings

HETEROCYCLIC COMPOUNDS

FIELD OF THE INVENTION

The present invention relates to novel N-substituted azaheterocyclic carboxylic acids and esters thereof in which a substituted alkyl chain forms part of the N-subsituent or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation. The invention also relates to the use of the present compounds for the treatment of insulin resistance in non-insulin-dependent diabetes mellitus (NIDDM) or aging, the present compounds knowing to interfere with neuropeptide containing C-fibres and hence inhibit the secretion and circulation of insulin antagonizing peptides like CGRP or amylin.

BACKGROUND OF THE INVENTION

The nervous system exerts a profound effect on the inflammatory response. Antidromic stimulation of sensory nerves results in localized vasodilation and increased vascular permeability (Janecso et al. Br. J. Pharmacol. 1967, 31, 138–151) and a similar response is observed following injection of peptides known to be present in sensory nerves. From this and other data it is postulated that peptides released from sensory nerve endings mediate many inflammatory responses in tissues like skin, joint, urinary tract, eye, meninges, gastro-intestinal and respiratory tracts. Hence inhibition of sensory nerve peptide release and/or activity, may be useful in treatment of, for example arthritis, dermatitis, rhinitis, asthma, cystitis, gingivitis, thrombophlelitis, glaucoma, gastro-intestinal diseases or migraine.

Further, the potent effects of CGRP on skeletal muscle glycogen synthase activity and muscle glucose metabolism, together with the notion that this peptide is released from the neuromuscular junction by nerve excitation, suggest that CGRP may play a physiological role in skeletal muscle glucose metabolism by directing the phosphorylated glucose away from glycogen storage and into the glycolytic and oxidative pathways (Rossetti et al. Am. J. Physiol. 264, E1–E10, 1993). This peptide may represent an important physiological modulator of intracellular glucose trafficking in physiological conditions, such as exercise, and may also contribute to the decreased insulin action and skeletal muscle glycogen synthase in pathophysiological conditions like NIDDM or aging-associated obesity (Melnyk et al. Obesity Res. 3, 337–344, 1995) where circulating plasma levels of CGRP are markedly increased. Hence inhibition of release and/or activity of the neuropeptide CGRP may be useful in the treatment of insulin resistance related to type 2 diabetes or aging.

In US Pat. No. 4,383,999 and No. 4,514,414 and in EP 236342 as well as in EP 231996 some derivatives of N-(4,4-disubstituted-3-butenyl)azaheterocyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake. Further, in WO 9107389 and WO 9220658, N-substituted azacyclic carboxylic acids are claimed as GABA uptake inhibitors. EP 221572 claims that 1-aryloxyalkylpyridine-3-carboxylic acids are inhibitors of GABA uptake.

DESCRIPTION OF THE INVENTION

The present invention relates to novel N-substituted azaheterocyclic carboxylic acids and esters thereof of formula I

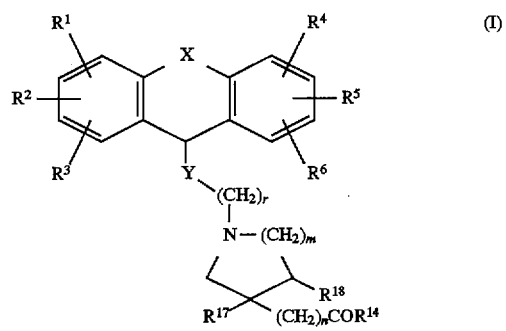

wherein $R^1$, $R^2$, $R^3$, $R^4$, $R^5$ and $R^6$ independently are hydrogen, halogen, trifluoromethyl, hydroxy, $C_{1-6}$—alkyl, $C_{1-6}$—alkoxy,—$NR^7R^8$ or —$SO_2NR^7R^8$ wherein $R^7$ and $R^8$ independently are hydrogen or $C_{1-6}$—alkyl; and X is completion of an optional bond, —$CH_2$—, —$CH_2CH_2$—, —CH=CH—, —O—, —$S(O)_z$— wherein z is 0, 1 or 2, or —$N(R^9)$—wherein $R^9$ is hydrogen or $C_{1-6}$—alkyl; and Y is —O—, —$S(O)_q$—wherein q is 0, 1 or 2, or —$N(R^{10})$—wherein $R^{10}$ is hydrogen or $C_{1-6}$—alkyl; and r is 1, 2, 3 or 4; and $R^{14}$ hydroxy, $C_{1-6}$—alkoxy or —$NR^{15}R^{16}$ wherein $R^{15}$ and $R^{16}$ independently are hydrogen or $C_{1-6}$—alkyl; and m is 1; and n is 1; and $R^{17}$ and $R^{18}$ each represents hydrogen;

or a pharmaceutically acceptable salt thereof.

The compounds of formula I may exist as geometric and optical isomers and all isomers and mixtures thereof are included herein. Isomers may be separated by means of standard methods such as chromatographic techniques or fractional crystallization of suitable salts.

Preferably, the compounds of formula I exist as the individual geometric or optical isomers.

The compounds according to the invention may optionally exist as pharmaceutically acceptable acid addition salts or—when the carboxylic acid group is not esterified—as pharmaceutically acceptable metal salts or—optionally alkylated—ammonium salts.

Examples of such salts include inorganic and organic acid addition salts such as hydrochloride, hydrobromide, sulphate, phosphate, acetate, fumarate, maleate, citrate, lactate, tartrate; oxalate or similar pharmaceutically acceptable inorganic or organic acid addition salts, and include the pharmaceutically acceptable salts listed in Journal of Pharmaceutical Science, 66, 2 (1977) which are hereby incorporated by reference.

The term "$C_{1-6}$—alkyl" as used herein, alone or in combination, refers to a straight or branched, saturated hydrocarbon chain having 1 to 6 carbon atoms such as e.g. methyl, ethyl, n-propyl, isopropyl, n-butyl, sec-butyl, isobutyl, tert-butly, n-pentyl, 2-methylbutyl, 3-methylbutyl, n-hexyl, 4-methylpentyl, neopentyl, n-hexyl, 1,2-dimethylpropyl, 2,2-dimethylpropyl and 1,2,2-trimethylpropyl.

The term "$C_{1-6}$—alkoxy" as used herein, alone or in combination, refers to a straight or branched monovalent substituent comprising a $C_{1-6}$—alkyl group linked through an ether oxygen having its free valence bond from the ether oxygen and having 1 to 6 carbon atoms e.g. methoxy, ethoxy, propoxy, isopropoxy, butoxy, pentoxy.

3

The term "halogen" means fluorine, chlorine, bromine or iodine.

Illustrative examples of compounds encompassed by the present invention include:

1-(2-(10,11-Dihydro-5H-dibenzo[a,d]cyclohepten-5-yloxy)ethyl)-3-pyrroli-dineacetic acid;

1-(2-(Dibenzo[a,d]cyclohepten-5-yloxy)ethyl)-3-pyrrolidineacetic acid;

1-(2-(9,10-Dihydroanthracen-9-yloxy)ethyl)-3-pyrrolidineacetic acid;

1-(2-(9H-Xanthen-9-yloxy)ethyl)-3-pyrrolidineacetic acid;

1-(2-(9H-Thioxanthen-9-yloxy)ethyl)-3-pyrrolidineacetic acid;

(1-(2-(10,11 -Dihydro-5H-dibenzo[a,d]cyclohepten-5-yloxy)-1 -ethyl) pyrrolidin-3-yl)acetic acid;

or a pharmaceutically acceptable salt thereof.

As used herein, the term "patient" includes any mammal which could benefit from treatment of neurogenic pain or inflammation or insulin resistance in NIDDM. The term particularly refers to a human patient, but is not intended to be so limited.

It has been demonstrated that the novel compounds of formula I inhibit neurogenic inflammation which involves the release of neuropeptides from peripheral and central endings of sensory C-fibres. Experimentally this can be demonstrated in animal models of formalin induced pain or paw oedema (Wheeler and Cowan, Agents Actions 1991, 34, 264–269) in which the novel compounds of formula I exhibit a potent inhibitory effect. Compounds of formula I may be used to treat all painful, hyperalgesic and/or inflammatory conditions in which C-fibers play a pathophysiological role by eliciting neurogenic pain or inflammation, i.e.:

Acutely painful conditions exemplified by migraine, post-operative pain, burns, bruises, post-herpetic pain (Zoster) and pain as it is generally associated with acute inflammation; chronic, painful and/or inflammatory conditions exemplified by various types of neuropathy (diabetic, post-traumatic, toxic), neuralgia, rheumatoid arthritis, spondylitis, gout, inflammatory bowel disease, prostatitis, cancer pain, chronic headache, coughing, asthma, chronic pancreatitis, inflammatory skin disease including psoriasis and autoimmune dermatoses, osteoporotic pain.

Further, it has been demonstrated that the compounds of general formula I improves the glucose tolerance in diabetic ob/ob mice and that this may result from the reduced release of CGRP from peripheral nervous endings. Hence the compounds of general formula I may be used in the treatment of NIDDM as well as aging-associated obesity. Experimentally this has been demonstrated by the subcutaneous administration of glucose into ob/ob mice with or without previous oral treatment with a compound of general formula I.

The compounds of formula I may be prepared by the following method:

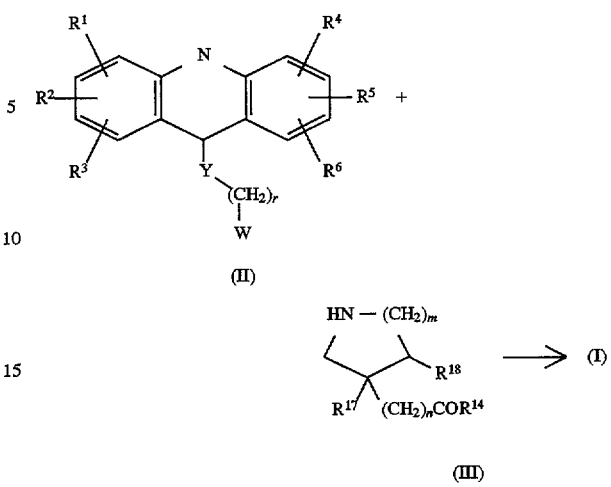

A compound of formula II wherein $R^1, R^2, R^3, R^4, R^5, R^6$, X, Y and r are as defined above and W is a suitable leaving group such as halogen, p-toluene sulphonate or mesylate may be reacted with an azaheterocyclic compound of formula III wherein $R^{14}$, $R^{18}$, n and m are as defined above. This alkylation reaction may be carried out in a solvent such as acetone, dibutylether, 2-butanone, methyl ethyl ketone, ethyl acetate, tetrahydrofuran (THF) or toluene in the presence of a base e.g. potassium carbonate and a catalyst, e.g. an alkali metal iodide at a temperature up to reflux temperature for the solvent used for e.g. 1 to 120 h. If esters have been prepared in which $R^{14}$ is alkoxy, compounds of formula I wherein $R^{14}$ is OH may be prepared by hydrolysis of the ester group, preferably at room temperature in a mixture of an aqueous alkali metal hydroxide solution and an alcohol such as methanol or ethanol, for example, for about 0.5 to 6 h.

Compounds of formula II and III may readily be prepared by methods familiar to those skilled in the art.

Under certain circumstances it may be necessary to protect the intermediates used in the above methods e.g. a compound of formula III with suitable protecting groups. The carboxylic acid group can, for example, be esterified. Introduction and removal of such groups is described in "Protective Groups in Organic Chemistry" J. F. W. McOrnie ed. (New York, 1973).

PHARMACOLOGICAL METHODS

Formalin induced pain or paw oedema

Values for in vivo inhibition of formalin induced pain or oedema for the compounds of the present invention were assessed in mice essentially by the method of Wheeler-Aceto and Cowan (Agents Action 1991, 34, 265–269).

About 20 g NMRI female mice were injected 20 μl 1% formalin into the left hind paw. The animals were then placed on a heated (31° C.) table, and the pain response was scored. After 1 h they were killed and bled. Left and right hind paws were removed and the weight difference between the paws was used as indication of the oedema response of the formalin injected paw.

Reduced release of CGRP ob/ob female mice, 16 weeks of age, where injected glucose (2 g/kg) subcutaneously. At times hereafter blood glucose was determined in tail venous blood by the glucose oxidase method. At the end of the study the animals were decapitated and trunck blood collected. Immunoreactive CGRP was determined in plasma by radio-immuno-assay. Two groups of animals were used. The one group was vehicle treated, whereas the other group received a compound of formula I via drinking water (100 mg/l) for five days before the test.

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula 1, conveniently given from 1 to 5 times daily, optionally in sustained release form. Usually, dosage forms suitable for oral administration tion comprise from about 0.5 mg to about 1000 mg, preferably from about 1 mg to about 500 mg of the compounds of formula I admixed with a pharmaceutical carrier or diluent.

The compounds of formula I may be administered in a pharmaceutically acceptable acid addition salt form or where possible as a metal or a lower alkylammonium salt. Such salt forms exhibit approximately the same order of activity as the free base forms.

This invention also relates to pharmaceutical compositions comprising a compound of formula I or a pharmaceutically acceptable salt thereof and, usually, such compositions also contain a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatin, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

If a solid carrier for oral administration is used, the preparation can be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

Generally, the compounds of this invention are dispensed in unit dosage form comprising 50–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet which may be prepared by conventional tabletting techniques contains

| Core: | |
|---|---|
| Active compound (as free compound or salt thereof) | 100 mg |
| Colloidal silicon dioxide (Areosil ®) | 1.5 mg |
| Cellulose, microcryst. (Avicel ®) | 70 mg |
| Modified cellulose gum (Ac-Di-Sol ®) | 7.5 mg |
| Magnesium stearate | |

| -continued | |
|---|---|
| Coating: | |
| HPMC approx. | 9 mg |
| *Mywacett ® 9-40 T approx. | 0.9 mg |

*Acylated monoglyceride used as plasticizer for film coating.

The route of administration may be any route which effectively transports the active compound to the appropriate or desired site of action, such as oral or parenteral e.g. rectal, transdermal, subcutaneous, intranasal, intramuscular, topical, intravenous, intraurethral, ophthalmic solution or an ointment, the oral route being preferred.

EXAMPLES

The process for preparing compounds of formula I and preparations containing them is further illustrated in the following examples, which, however, are not to be construed as limiting.

Hereinafter, TLC is thin layer chromatography, $CDCl_3$ is deuterio chloroform and $DMSO-d_6$ is hexadeuterio dimethylsulfoxide. The structures of the compounds are confirmed by either elemental analysis or NMR, where peaks assigned to characteristic protons in the title compounds are presented where appropriate. $^1$HNMR shifts ($\delta_H$) are given in parts per million (ppm). M.p. is melting point and is given in ° C. and is not corrected. Column chromatography was carried out using the technique described by W.C. Still et al, J. Org. Chem. (1978), 43, 2923–2925 on Merck silica gel 60 (Art. 9385). Compounds used as starting materials are either known compounds or compounds which can readily be prepared by methods known per se.

EXAMPLE 1

(1-(2-(10, 11 -Dihydro-5H-dibenzo[a,d]cyclohepten-5-yloxy)-1-ethyl) pyrrolidin-3-yl)acetic acid hemimaleate

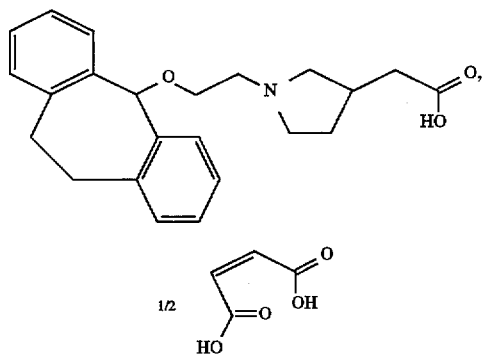

10, 11 -Dihydro-5H-dibenzo[a,d]cyclohepten-5-ol (21.0 g, 0.10 mol) was dissolved in tetrahydrofuran (250 ml). Sodium hydride, 60% (4.8 g, 0.12 mol) was added in portions at room temperature. The mixture was stirred for 0.5 h, ethyl bromoacetate (25.05 g, 0.15 mol) dissolved in tetrahydrofuran (50 ml) was added dropwise and the reaction was stirred for 16 h. Lithium aluminium hydride (4.56 g, 0.12 mol) was added carefully to the stirred solution, while keeping the temperature <30° C. by cooling on an ice-bath. After the addition was complete, stirring was continued for 0.5 h. Ethyl acetate (150 ml) was added carefully, followed by water (8.6 ml). The mixture was filtered, the flitrate was dried ($MgSO_4$) and concentrated in vacuo. The remaining oil was purified by column chromatography on silica gel (480 g), using a mixture of toluene and acetone (97.5:2.5) as eluent. This afforded 14.1 g 2-(10,11-dihydro-5H-dibenzo-[a,d]cyclohepten-5-yloxy)-1-ethenol as an oil.

The above crude alcohol (2.54 g, 10 mmol) was dissolved in dry tetrahydrofuran (50 ml), triethylamine (2.02 g, 20 mmol) was added and methanesulfonyl chloride (1.72 g, 15 mmol) was added dropwise. The mixture was stirred for 1 h, filtered and evaporated in vacuo. The residue was dissolved in 2-butanone (100 ml), pyrrolidin-3-ylacetic acid methyl ester acetate (2.43 g, 12 mmol) and potassium carbonate (5.53 g, 40.0 mmol) were added and the mixture was heated at reflux temperature for 16 h. The reaction mixture was concentrated in vacuo, redissolved in diethyl ether (60 ml) and the ether solution washed with water (2 × 50 ml). Evaporation of the solvent in vacuo afforded an oil which was subjected to column chromatography on silica gel (240 g) using a mixture of heptane, ethyl acetate and triethylamine (67.5:30:2.5) as eluent to furnish 1.11 g (1-(2-(10,11-dihydro-5H-dibenzo[a,d]cyclohepten-5-yloxy)ethyl)pyrrolidin-3-yl) acetic acid methyl ester as an oil.

The above ester (0.95 g, 2.50 mmol) was dissolved in ethanol (12.5 ml). 2N Sodium hydroxide (4.5 ml) was added and the mixture was stirred at room temperature for 1.5 h. Water (20 ml) was added and the ethanol was evaporated in vacuo. The aqueous solution was adjusted to pH 6 by careful addition of acetic acid and extracted with dichloromethane (2 × 30 ml). The combined organic extracts were washed with water (30 ml), dried ($MgSO_4$) and concentrated in vacuo. The remainder (0.52 g, 1.42 mmol) was dissolved in tetrahydrofuran (10 ml) and a solution of maleic acid (0.083 g, 0.71 mmol) in diethyl ether (20 ml) was added slowly. The precipitate was filtered off, washed with a small amount of ether and dried to afford 0.44 g of the title compound as an amorphous powder.

Calculated for $C_{23}H_{27}N_3$, 0.5 $C_4H_4O_4$, 0.5 $H_2O$: C, 69.43%; H, 6.99%, N, 3.24%; Found: C, 69.23%; H, 7.06%, N, 2.88%. HPLC retention time = 16.13 minutes (5 μm C18 4 × 250 mm column, eluting with a 20–80% gradient of 0.1% trifluoroacetic acid/acetonitrile and 0.1% trifluoroacetic acid/water over 25 minutes at 35° C.).

We claim:

1. A compound of formula I

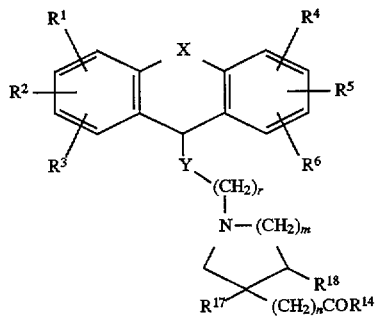

wherein $R^1$, $R^2$, $R^3$, $R^4$, $R^5$ and $R^6$ independently are hydrogen, halogen, trifluoromethyl, hydroxy, $C_{1-6}$—alkyl, $C_{1-6}$—alkoxy, -$NR^7R^8$ or -$SO_2NR^7R^8$ wherein $R^7$ and $R^8$ independently are hydrogen or $C_{1-6}$-alkyl;

X is completion of an optional bond, -$CH_2$-, —$CH_2CH_2$—, —CH=CH—, -O-, -S(O)$_z$- wherein z is 0, 1 or 2, or —N($R^9$)— wherein $R^9$ is hydrogen or $C_{1-6}$-alkyl;

Y is -O-, -S(O)$_q$- wherein q is 0, 1 or 2, or -N($R^{10}$)- wherein $R^{10}$ is hydrogen or $C_{1-6}$-alkyl;

r is 1, 2, 3 or 4;

$R^{14}$ is hydroxy, $C_{1-6}$-alkoxy or -$NR^{15}R^{16}$ wherein $R^{15}$ and $R^{16}$ independently are hydrogen or $C_{1-6}$-alkyl;

m is 1;

n is 1; and $R^{17}$ and $R^{18}$ each are hydrogen; or a pharmaceutically acceptable salt thereof.

2. A compound according to claim 1 wherein $R^1$, $R^2$, $R^3$, $R^4$, $R^5$ and $R^6$ independently are hydrogen, halogen, trifluoromethyl or $C_{1-6}$-alkoxy.

3. A compound according to claim 2 wherein $R^1$, $R^2$, $R^3$, $R^4$, $R^5$ and $R^6$ are hydrogen.

4. A compound according to claim 1 wherein X is —$CH_2CH_2$— or -S(O)$_z$- wherein Z is 0 or 1.

5. A compound according to claim 4 wherein X is —$CH_2$—$CH_2$—.

6. A compound according to claim 1 wherein Y is —O—.

7. A compound according to claim 1 wherein r is 2 or 3.

8. A compound according to claim 1 wherein $R^{14}$ is hydroxy.

9. A compound according to claim 1 which is:

1-(2-(10,11-Dihydro-5H-dibenzo [a,d]cyclohepten-5-yloxy)ethyl)-3-pyrrolidineacetic acid; or a pharmaceutically acceptable salt thereof.

10. A compound according to claim 1 which is:

1-(2-(Dibenzo[a,d]cyclohepten-5-yloxy)ethyl)-3-pyrrolidineacetic acid; or a pharmaceutically acceptable salt thereof.

11. A compound according to claim 1 which is:

1-(2-(9,10-Dihydroanthracen-9-yloxy)ethyl)-3-pyrrolidineacetic acid; or a pharmaceutically acceptable salt thereof.

12. A compound according to claim 1 which is:

1-(2-(9H-Xanthen-9-yloxy)ethyl)-3-pyrrolidineacetic acid; or a pharmaceutically acceptable salt thereof.

13. A compound according to claim 1 which is:

1-(2-(9H-Thioxanthen-9-yloxy)ethyl)-3-pyrrolidineacetic acid; or a pharmaceutically acceptable salt thereof.

14. A compound according to claim 1 which is:

1-(2- (10,11-Dihydro-5H-dibenzo [a,d] cyclohepten-5-yloxy)-1-ethyl)pyrrolidin-3 -yl) acetic acid; or a pharmaceutically acceptable salt thereof.

15. A pharmaceutical composition comprising as active component a compound according to claim 1 together with a pharmaceutically carrier or diluent.

16. The pharmaceutical composition according to claim 15, wherein the compound is present in an amount between 0.5 mg and 1000 mg per unit dose.

17. A method of treating neurogenic intimation, migraine, diabetic neuropathy or rheumatoid arthritis in a subject in need of such treatment comprising administering to the subject an effective amount of a compound according to claim 1.

18. A method of treating insulin resistance in a subject in need of such treatment comprising administering to the subject an effective amount of a compound according to claim 1.

19. A method of treating neurogenic intimation, migraine, diabetic neuropathy or rheumatoid arthritis in a subject in need of such treatment comprising administering to the subject a pharmaceutical composition according to claim 15.

20. A method of treating insulin resistance in a subject in need of such treatment comprising administering to the subject a pharmaceutical composition according to claim 15.

* * * * *